United States Patent
Kawasaki et al.

(10) Patent No.: US 11,678,902 B2
(45) Date of Patent: Jun. 20, 2023

(54) ENERGY CONTROL DEVICE AND TREATMENT SYSTEM

(71) Applicant: OLYMPUS CORPORATION, Hachioji (JP)

(72) Inventors: Minoru Kawasaki, Tokyo (JP); Yoshihiro Tsubuku, Fuchu (JP); Gen Kato, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 1183 days.

(21) Appl. No.: 16/257,927

(22) Filed: Jan. 25, 2019

(65) Prior Publication Data

US 2019/0150975 A1 May 23, 2019

Related U.S. Application Data

(63) Continuation of application No. PCT/JP2016/071742, filed on Jul. 25, 2016.

(51) Int. Cl.
*A61B 17/32* (2006.01)
*A61B 17/00* (2006.01)
*A61B 90/90* (2016.01)

(52) U.S. Cl.
CPC ...... *A61B 17/320092* (2013.01); *A61B 17/32* (2013.01); *A61B 90/90* (2016.02);
(Continued)

(58) Field of Classification Search
CPC .... A61B 17/320068; A61B 17/320088; A61B 17/320092; A61B 2017/00017;
(Continued)

(56) References Cited

U.S. PATENT DOCUMENTS

2009/0036913 A1  2/2009 Wiener et al.
2009/0036914 A1  2/2009 Houser
(Continued)

FOREIGN PATENT DOCUMENTS

JP  2010-535087 A  11/2010
JP  2010-535090 A  11/2010
(Continued)

OTHER PUBLICATIONS

Oct. 25, 2016 Search Report issued in International Patent Application No. PCT/JP2016/071742.
(Continued)

*Primary Examiner* — Todd J Scherbel
(74) *Attorney, Agent, or Firm* — Oliff PLC (57) ABSTRACT

An energy control device supplies power to an ultrasonic treatment instrument including an end effector performing treatment using ultrasonic vibration generated by an ultrasonic transducer. The energy control device includes an energy source configured to output the power to the ultrasonic transducer, and an integrated circuit. The integrated circuit is configured to: acquire a resonance frequency of a vibration system including the ultrasonic transducer; calculate an initial feature value relating to the resonance frequency after a start of an output of the power; set a threshold based on the initial feature value; and perform causing the energy source to stop or reduce the output of the power to the ultrasonic transducer based on a relationship between the resonance frequency and the threshold, or notifying the relationship between the resonance frequency and the threshold.

19 Claims, 5 Drawing Sheets

(52) U.S. Cl.
CPC ............... *A61B 2017/00017* (2013.01); *A61B 2017/00115* (2013.01); *A61B 2017/00123* (2013.01); *A61B 2017/320094* (2017.08)

(58) Field of Classification Search
CPC ........... A61B 2017/00075; A61B 2017/00106; A61B 2017/00119; A61B 2017/00123
See application file for complete search history.

(56) References Cited

U.S. PATENT DOCUMENTS

| | | |
|---|---|---|
| 2009/0259244 A1 | 10/2009 | Shimizu |
| 2011/0082486 A1 | 4/2011 | Messerly et al. |
| 2012/0209303 A1* | 8/2012 | Frankhouser ...... A61B 17/3476 606/169 |
| 2012/0310262 A1 | 12/2012 | Messerly et al. |
| 2012/0310263 A1 | 12/2012 | Messerly et al. |
| 2012/0310264 A1 | 12/2012 | Messerly et al. |
| 2013/0267975 A1* | 10/2013 | Timm .................... H01H 23/28 606/169 |
| 2013/0282038 A1* | 10/2013 | Dannaher ...... A61B 17/320092 606/1 |
| 2013/0282039 A1 | 10/2013 | Wiener et al. |
| 2015/0182251 A1 | 7/2015 | Messerly et al. |
| 2015/0196318 A1 | 7/2015 | Messerly et al. |
| 2015/0257780 A1 | 9/2015 | Houser |
| 2015/0327883 A1 | 11/2015 | Messerly et al. |
| 2015/0328484 A1 | 11/2015 | Messerly et al. |
| 2017/0202595 A1* | 7/2017 | Shelton, IV ........... A61B 18/00 |

FOREIGN PATENT DOCUMENTS

| | | |
|---|---|---|
| JP | 2013-541987 A | 11/2013 |
| JP | 2014054546 A | 3/2014 |
| WO | 2012/044600 A2 | 4/2012 |

OTHER PUBLICATIONS

Nov. 12, 2019 Office Action issued in Japanese Patent Application No. 2018-530215.

* cited by examiner

F I G. 5

ENERGY CONTROL DEVICE AND TREATMENT SYSTEM

CROSS-REFERENCE TO RELATED APPLICATIONS

This application is a Continuation Application of PCT Application No. PCT/JP2016/071742, filed Jul. 25, 2016, the entire contents of which are incorporated herein by reference.

BACKGROUND OF THE INVENTION

1. Field of the Invention

The present invention relates to an energy control device for an ultrasonic treatment instrument and a treatment system including the same.

2. Description of the Related Art

There is known an ultrasonic treatment instrument that grasps a living tissue to be treated with a pair of grasping pieces and ultrasonically vibrates one of the grasping pieces to perform coagulation, incision, or the like of the grasped living tissue. An example of such an ultrasonic treatment instrument is disclosed in International Publication No. 2012/044600. A resonance frequency of a vibration system including a grasping piece that ultrasonically vibrates decreases as temperature rises. Therefore, when the resonance frequency of the vibration system is acquired, it is possible to grasp a state of treatment that is being performed to a certain extent. In the ultrasonic treatment instrument disclosed in the above literature, a control device detects a resonance frequency of the vibration system that ultrasonically vibrates, and determines that grasping piece has become sufficiently high temperature when the resonance frequency has fallen below a certain threshold, and reduces an amplitude of ultrasonic vibration.

It is not preferable to continue the vibration in the ultrasonic treatment instrument that grasps a living tissue with the pair of grasping pieces to perform the treatment of the tissue by ultrasonic vibration even after the treatment has been completed and the tissue has been divided. If the grasping piece vibrates in a state where the pair of grasping pieces is in direct contact with each other, there is a risk that the grasping piece may be damaged. A technique of apprehending the temperature of the grasping piece by detecting the resonance frequency of the vibration system as disclosed in the above literature can also be used to detect division of the tissue to be treated, for example, to stop the output after the division.

BRIEF SUMMARY OF THE INVENTION

According to an aspect of the present invention, an energy control device supplies power to an ultrasonic treatment instrument including an end effector performing treatment using ultrasonic vibration generated by an ultrasonic transducer. The energy control device includes an energy source, and at least one integrated circuit. The energy source is configured to output the power to the ultrasonic transducer. The integrated circuit is configured to: acquire a resonance frequency of a vibration system including the ultrasonic transducer; calculate an initial feature value relating to the resonance frequency after a start of an output of the power; set a threshold based on the initial feature value; and perform at least one of causing the energy source to stop or reduce the output of the power to the ultrasonic transducer based on a relationship between the resonance frequency and the threshold and notifying the relationship between the resonance frequency and the threshold.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Configuration of Treatment System

Figure 1:
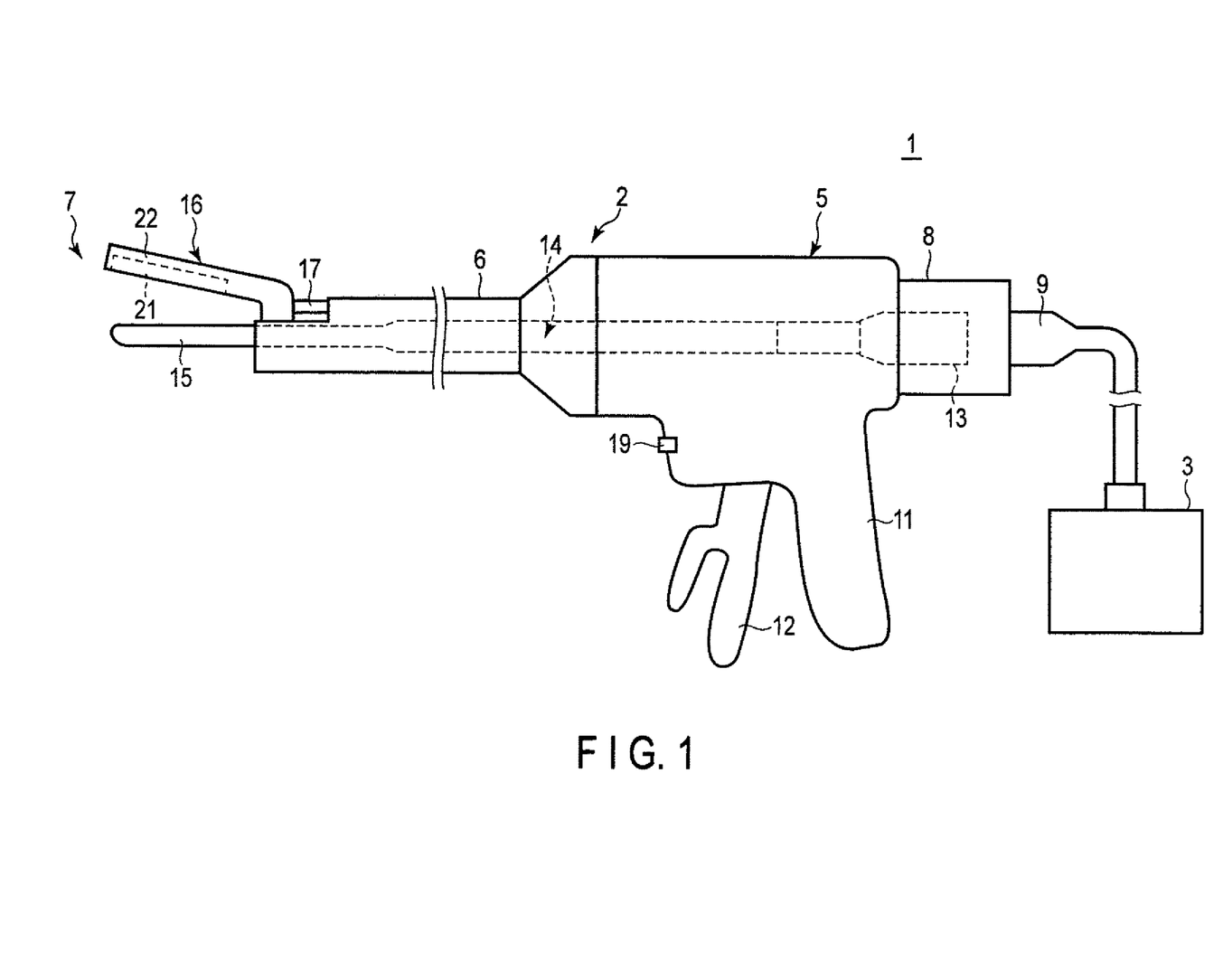
FIG. 1 is a view illustrating an example of an outline of a treatment system according to one embodiment.

One embodiment of the present invention will be described with reference to the drawings. The present embodiment relates to a treatment system that uses ultrasonic vibration to perform treatment of a living tissue. FIG. 1 is a view illustrating a treatment system 1. As illustrated in FIG. 1, the treatment system 1 includes an ultrasonic treatment instrument 2 and an energy control device 3 that supplies power to the ultrasonic treatment instrument 2.

The ultrasonic treatment instrument 2 includes a housing 5, a shaft 6 connected to the housing 5, and an end effector 7 provided at an end of the shaft 6. A side on which the end effector 7 is provided will be referred to as a distal end side and a side on which the housing 5 is provided will be referred to as a proximal end side. The housing 5 is provided with a grip 11 and a handle 12. A user grasps the grip 11 to hold the ultrasonic treatment instrument 2. The handle 12 is configured to be opened and closed with respect to the grip 11.

An ultrasonic transducer unit 8 is provided on the proximal end side of the housing 5. The ultrasonic transducer unit 8 has an ultrasonic transducer 13 including at least one piezoelectric element. The ultrasonic transducer unit 8 is detachably connected to the energy control device 3 via a cable 9. The ultrasonic transducer 13 vibrates as AC power is supplied from the energy control device 3 to the ultrasonic transducer 13 of the ultrasonic transducer unit 8.

A rod member 14 is connected to the ultrasonic transducer 13 of the ultrasonic transducer unit 8. The rod member 14 passes through the inside of the housing 5 and the shaft 6 and reaches the end effector 7. That is, a distal end portion of the rod member 14 forms a first grasping piece 15 of the end effector 7. The rod member 14 is made of a material having a high vibration transmissibility such as a titanium alloy. The ultrasonic vibration generated by the ultrasonic transducer 13 is transmitted to the rod member 14. As a result, the first grasping piece 15 vibrates. The first grasping piece 15 vibrates at a frequency corresponding to arbitrarily designed resonance of a vibration system. This resonance frequency is, for example, about several tens of kHz although not limited thereto, and may be, for example, 46 kHz to 48 kHz (about 47 kHz).

A second grasping piece 16 is attached to a distal end portion of the shaft 6 so as to be open or closed with respect to the first grasping piece 15. The second grasping piece 16 and the handle 12 are connected by a movable member 17 passing through the inside of the shaft 6. The movable member 17 moves to the distal end side or the proximal end side by opening or closing the handle 12 with respect to the grip 11, and the second grasping piece 16 rotates with respect to the shaft 6 to be open and closed with respect to the first grasping piece 15. In this manner, the first grasping piece 15 and the second grasping piece 16 of the end effector 7 are open or closed along with the opening or closing operation of the handle 12 with respect to the grip 11. The end effector 7 is configured to grasp a living tissue to be treated by the first grasping piece 15 and the second grasping piece 16.

The second grasping piece 16 includes a pad member 21 and a holder member 22 to which the pad member 21 is attached. The pad member 21 is made of a resin such as polytetrafluoroethylene (PTFE). In a state where the first grasping piece 15 and the second grasping piece 16 are closed, the pad member 21 of the second grasping piece 16 is in contact with the first grasping piece 15, and the other portion of the second grasping piece 16 is not in contact with the first grasping piece 15.

Figure 2A:
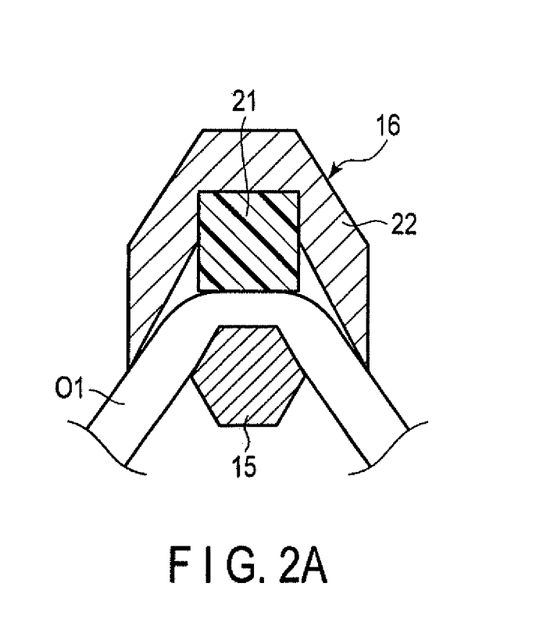
FIG. 2A is a view illustrating a schematic cross section perpendicular to a longitudinal axis of an end effector regarding the end effector and a tissue to be treated according to one embodiment.
Figure 2B:
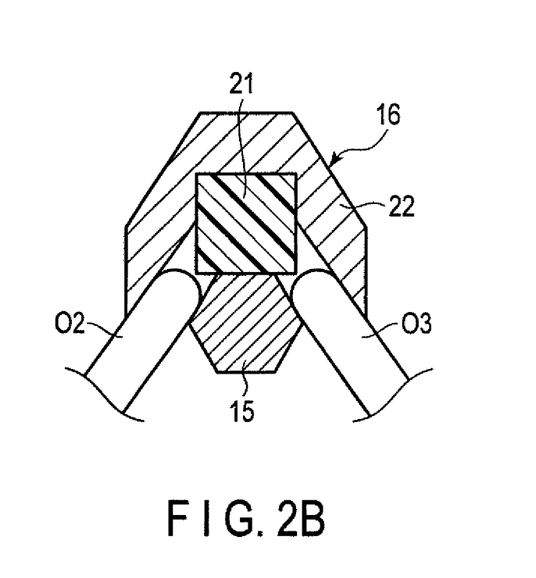
FIG. 2B is a view illustrating a schematic cross section perpendicular to the longitudinal axis of the end effector regarding the end effector and the tissue to be treated according to one embodiment.

FIGS. 2A and 2B are views illustrating cross sections perpendicular to longitudinal axes of the first grasping piece 15 and the second grasping piece 16 when using the ultrasonic treatment instrument 2. FIG. 2A illustrates a state where a tissue O1 to be treated is sandwiched between the first grasping piece 15 and the second grasping piece 16. The ultrasonic treatment instrument 2 can incise the tissue O1 while coagulating the tissue O1 as the first grasping piece 15 ultrasonically vibrates with the tissue O1 sandwiched between the first grasping piece 15 and the second grasping piece 16. FIG. 2B illustrates a state where the tissue is divided into a first tissue piece O2 and a second tissue piece O3. At this time, the pad member 21 is in contact with the first grasping piece 15.

The housing 5 is provided with an operation button 19. An operation to switch on and off of the supply of power from the energy control device 3 to the ultrasonic transducer unit 8 is input to the operation button 19. Incidentally, the treatment system 1 may be provided with a foot switch having the same function as the operation button 19 instead of the operation button 19 or together with the operation button 19.

Figure 3:
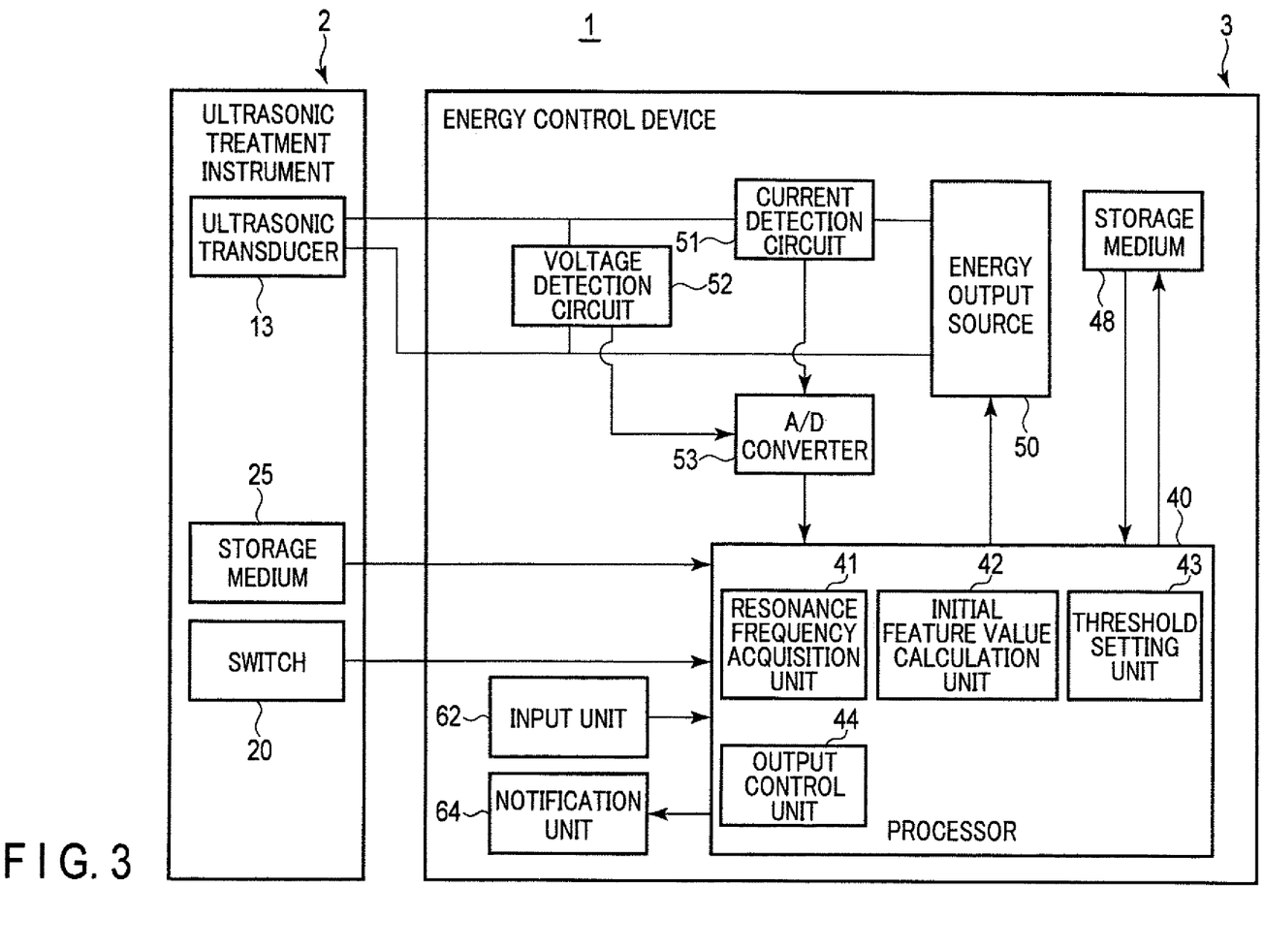
FIG. 3 is a block diagram illustrating an example of a configuration relating to supply of power from an energy control device to an ultrasonic treatment instrument according to one embodiment.

FIG. 3 is a diagram schematically illustrating a configuration example of the treatment system 1 relating to the supply of power from the energy control device 3 to the ultrasonic treatment instrument 2.

As illustrated in FIG. 3, the ultrasonic treatment instrument 2 is provided with the ultrasonic transducer 13, a switch 20, and a storage medium 25. The ultrasonic transducer 13 is an ultrasonic transducer serving as a vibration source provided in the ultrasonic transducer unit 8 described above. The switch 20 is provided inside the housing 5 of the ultrasonic treatment instrument 2. The switch 20 is switched between an on-state and an off-state as the operation is input by the operation button 19. Further, information on the treatment instrument is stored in the storage medium 25.

The energy control device 3 includes a processor 40 controlling an operation of the treatment system 1 and a storage medium 48. The processor 40 operates based on, for example, a program stored in the storage medium 48, and controls an operation of each unit of the energy control device 3. In the storage medium 48, a processing program to be used by the processor 40, a parameter, a table, and the like to be used for computation performed by the processor 40 are stored.

Further, the energy control device 3 includes an energy output source 50, a current detection circuit 51, a voltage detection circuit 52, and an A/D converter 53. The energy output source 50 supplies AC power to the ultrasonic transducer 13 of the ultrasonic treatment instrument 2. The energy output source 50 outputs power under the control of the processor 40. The current detection circuit 51 detects a current value of an output current I from the energy output source 50 to the ultrasonic transducer 13. The voltage detection circuit 52 detects a voltage value of an output voltage V from the energy output source 50 to the ultrasonic transducer 13. Analog signals output from the current detection circuit 51 and the voltage detection circuit 52 are converted into digital signals via the A/D converter 53 and the converted signals are transmitted to the processor 40.

The energy control device 3 further includes an input unit 62 and a notification unit 64. The input unit 62 is a part that receives an input of a user with respect to the energy control device 3. The input unit 62 includes, for example, a touch panel, a button switch, a keyboard, or the like. The notification unit 64 is a part that notifies the user of information. The notification unit 64 includes, for example, a display, a speaker, or the like.

The energy control device 3 according to the present embodiment performs the following operation. That is, when the switch 20 of the ultrasonic treatment instrument 2 is turned on, the supply of power to the ultrasonic treatment instrument 2 is started with detection of such an on-state. Along with the treatment, the temperature of the first grasping piece 15 of the ultrasonic treatment instrument 2 rises, and the resonance frequency of the vibration system having temperature dependence decreases. The energy control device 3 adjusts an output frequency in accordance with the changing resonance frequency. Further, a progress state of the treatment is determined based on the resonance frequency, and the output is stopped or the like. The processor 40 performs computation relating to the operation of the energy control device 3 as described above.

The processor 40 executes functions as a resonance frequency acquisition unit 41, an initial feature value calculation unit 42, a threshold setting unit 43, and an output control unit 44. The resonance frequency acquisition unit 41 acquires a resonance frequency of the vibration system including the ultrasonic transducer 13, the rod member 14, and the like of the ultrasonic treatment instrument 2. The resonance frequency acquisition unit 41 can acquire the resonance frequency based on an output current and an output voltage from the energy output source 50 supplied to the ultrasonic transducer 13. The initial feature value calculation unit 42 calculates a value relating to the resonance frequency of the vibration system in an initial stage of the operation after the output of power from the energy output source 50 has been started as an initial feature value. The threshold setting unit 43 sets an operation threshold based on the initial feature value. The output control unit 44 controls the output of the energy output source 50. Such control includes detection of a state of the switch 20 and controlling of the output of the energy output source 50 based on the detection result. Such control includes comparison between the resonance frequency of the vibration system and the operation threshold to change the output based on the comparison result. For example, when the resonance frequency has fallen below the operation threshold, the output control unit 44 causes the energy output source 50 to stop or reduce the output of power to the ultrasonic transducer 13, or notifies that the resonance frequency has fallen below the operation threshold.

The processor 40 includes an integrated circuit such as a central processing unit (CPU), an application specific integrated circuit (ASIC), and a field programmable gate array (FPGA). The processor 40 may be constituted by one integrated circuit or the like, or a combination of a plurality of integrated circuits or the like. Such operations of the integrated circuit are performed in accordance with programs recorded in, for example, the storage medium 48 or a recording area in the integrated circuit.

Operation of Treatment System

The operation of the treatment system 1 according to the present embodiment will be described. When an object to be treated such as a living tissue is treated using the treatment system 1, the user holds the grip 11 and the handle 12, and inserts the end effector 7 into a body cavity such as an abdominal cavity. The user arranges a living tissue or the like to be treated between the first grasping piece 15 and the second grasping piece 16, and closes the handle 12 with respect to the grip 11. As a result, the second grasping piece 16 is closed with respect to the first grasping piece 15, and the living tissue is grasped between the first grasping piece 15 and the second grasping piece 16.

In this state, the user turns on the operation button 19. At this time, the processor 40 detects that the switch 20 has been turned on. The output control unit 44 of the processor 40 causes the energy output source 50 to start outputting the power to the ultrasonic transducer 13. As a result, ultrasonic vibration is generated by the ultrasonic transducer 13, and the generated ultrasonic vibration is transmitted to the first grasping piece 15 via the rod member 14. When the first grasping piece 15 ultrasonically vibrates in a state where the tissue to be treated is grasped between the first grasping piece 15 and the second grasping piece 16, frictional heat is generated between the first grasping piece 15 and the grasped tissue. Due to the frictional heat, the tissue is incised at the same time of being coagulated.

As illustrated in FIG. 2B, a state where the first grasping piece 15 and the second grasping piece 16 are in contact with each other is formed in a situation where the tissue to be treated has been cut. When the first grasping piece 15 continues ultrasonic vibration in this state, the pad member 21 and the like of the second grasping piece 16 is likely to be damaged. Therefore, in the present embodiment, when the processor 40 detects the situation where the tissue has been cut, the processor 40 stops or reduce the supply of power to the ultrasonic transducer 13 from the energy output source 50, and stops or reduces the output of the ultrasonic treatment instrument 2. The processor 40 may notify the user of the detection result when detecting the situation where the tissue has been cut.

Figure 4:
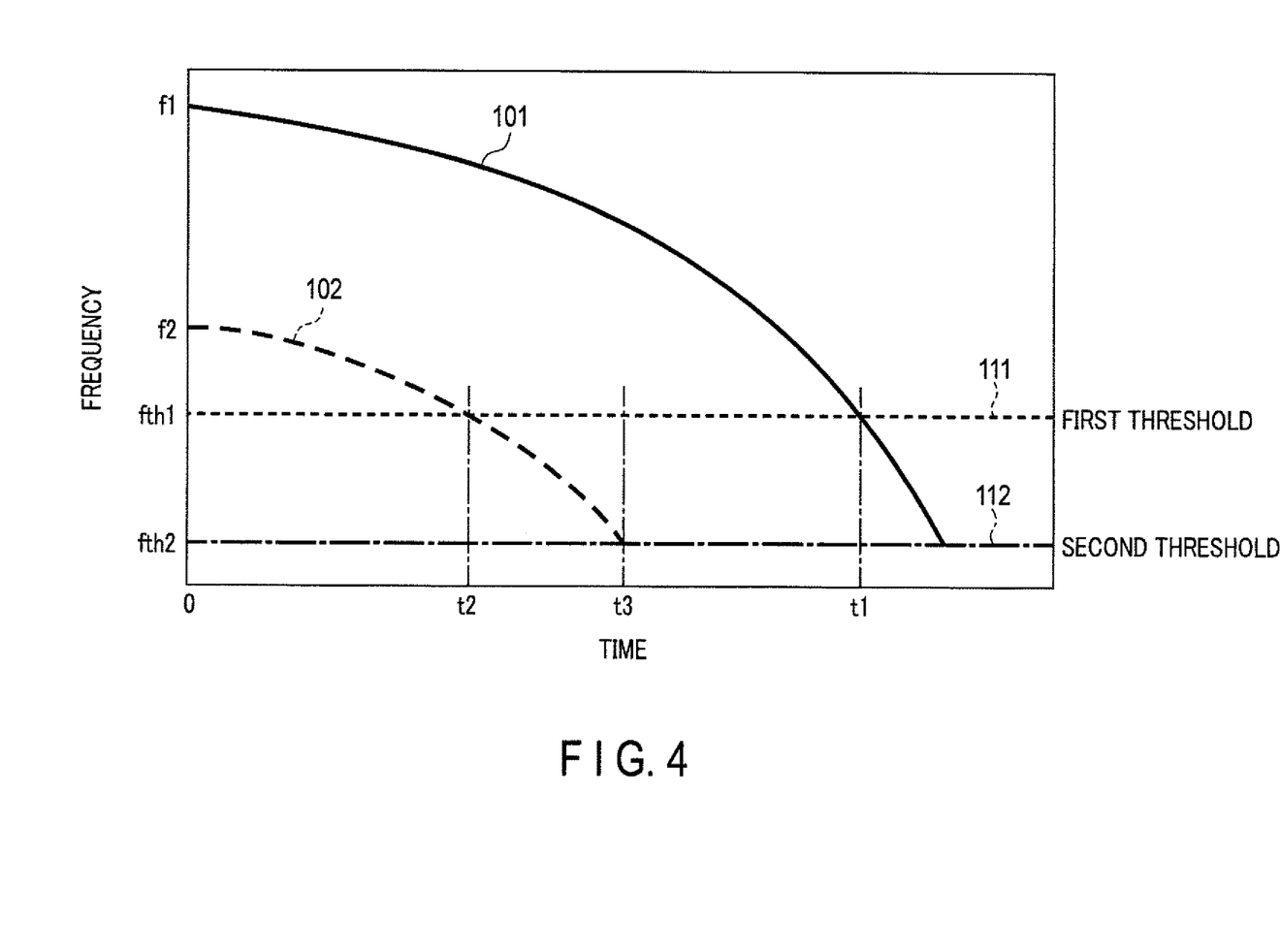
FIG. 4 is a view for describing a frequency change with respect to an elapsed time and a threshold for determination.

An operation relating to the stop or reduction of output according to the present embodiment will be described with reference to a schematic view illustrated in FIG. 4. FIG. 4 schematically illustrates a change of a resonance frequency of the vibration system including the ultrasonic transducer 13 with respect to an elapsed time from an output start. At the time of treatment, the temperature of the first grasping piece 15 gradually increases. Along with such a temperature rise, the resonance frequency of the vibration system including the first grasping piece 15 decreases. In the present embodiment, the processor 40 stops or reduces the output when the resonance frequency has fallen below the predetermined threshold or notifies the user of the fact that the resonance frequency is decreasing (the temperature is rising) based on the decrease in the resonance frequency.

For example, the resonance frequency which was at a frequency f1 at a treatment start decreases with a lapse of time as indicated by a solid line 101 in FIG. 4. The processor 40 sets a first threshold at a frequency fth1 as indicated by a broken line 111, for example. When the resonance frequency of the vibration system has fallen below the first threshold, the processor 40 stops or reduces the output or notifies that the resonance frequency has fallen below the first threshold or the like. In the example illustrated in FIG. 4, the processor 40 stops or reduces the output or notifies that the resonance frequency has fallen below the first threshold or the like when an elapsed time from the start of the treatment is t1.

There is a case where different parts are subjected to treatment consecutively within a short period of time depending on a procedure. In such a case, the temperature of the first grasping piece 15 when starting second treatment is higher than the temperature of the first grasping piece 15 when starting first treatment. For example, in the example illustrated in FIG. 4, the resonance frequency changes as indicated by the solid line 101 during the first treatment, and the resonance frequency changes as indicated by a broken line 102 during the second treatment. Even during such second treatment, the output is stopped when an elapsed time from a treatment start is, for example, t2 which is less than half of t1 when the output is stopped, for example, when the resonance frequency has fallen below the first threshold (frequency fth1) indicated by the broken line 111. However, there is a case where it is difficult to perform sufficient treatment if the duration of the output in the second treatment is, for example, t2 which is less than half of t1 while the duration of the output in the first treatment is t1. Therefore, for example, the threshold for the stop of the output is determined based on the initial feature value relating to the resonance frequency at the start of output in the present embodiment.

For example, when the initial feature value is a value of the resonance frequency at the start of treatment, the resonance frequency at the start of treatment is a frequency f1 in the first treatment in the example illustrated in FIG. 4, and based on this value, the first threshold is set to the frequency fth1 as indicated by the broken line 111. On the other hand, the resonance frequency at the start of treatment is a frequency f2 lower than the frequency f1 in the second treatment, and based on this value, the second threshold is set to a frequency fth2 lower than the frequency fth1 as indicated by a dashed-dotted line 112. As a result, the duration of the output in the second treatment is not t2 when the operation threshold is the first threshold (frequency fth1) but t3 when the operation threshold is the second threshold (frequency fth2). Here, t3 is longer than t2. Thus, the duration of the output is appropriately adjusted by setting the operation threshold based on the initial feature value.

The frequencies f1, f2, fth1, and fth2 are values in the range of about 40 kHz to 60 kHz, for example. The frequencies f1, f2, fth1, and fth2 may be values in the range of 46 kHz to 48 kHz when the resonance frequency of the vibration system including the ultrasonic transducer 13 and the rod member 14 is 46 kHz to 48 kHz as described above as an example. The times t1, t2, and t3 are values in the range of, for example, several seconds to a dozen or so seconds.

Output Control Process

Figure 5:
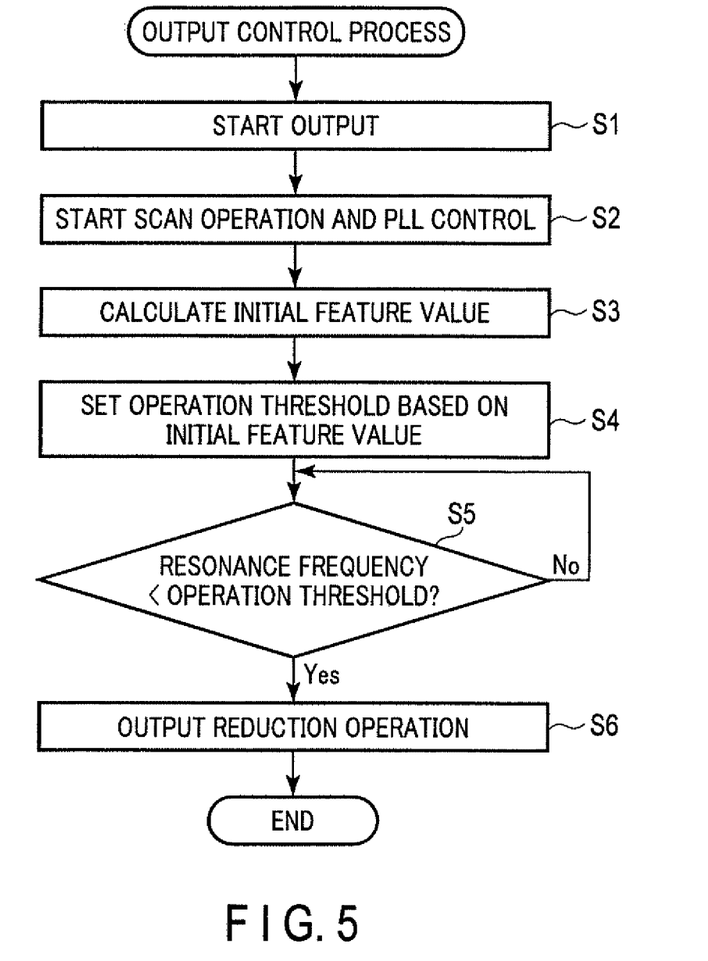
FIG. 5 is a flowchart schematically illustrating an example of an output control process according to one embodiment.

The control of the output by the processor 40 will be described with reference to the flowchart illustrated in FIG. 5. An output control process illustrated in FIG. 5 starts, for example, when the operation button 19 is pushed by the user.

In Step S1, the output control unit 44 of the processor 40 causes the energy output source 50 to start outputting ultrasonic waves. The energy output source 50 supplies predetermined power to the ultrasonic transducer 13 under the control of the processor 40.

In Step S2, the processor 40 causes the energy output source 50 to perform a scan operation of an output frequency, and then, starts control using a phase locked loop (PLL) to cause the energy output source 50 to output power. That is, the output control unit 44 of the processor 40 causes the energy output source 50 to output power while gradually changing the output frequency from a high frequency to a low frequency, for example, in the range including the resonance frequency of the vibration system including the ultrasonic transducer 13. The resonance frequency acquisition unit 41 of the processor 40 acquires a current and a voltage at this time and acquires a frequency at which phases of the current and the voltage coincide with each other, that is, the resonance frequency of the vibration system. The processor 40 uses the acquired resonance frequency as an initial value and makes the output frequency follow the resonance frequency of the vibration system using the PLL thereafter. Subsequently, the PLL is used to vibrate the first grasping piece 15 at the resonance frequency. In general, the temperature of the first grasping piece 15 gradually increases so that the resonance frequency of the vibration system gradually decreases as illustrated in FIG. 4.

In Step S3, the initial feature value calculation unit 42 of the processor 40 calculates the initial feature value based on the resonance frequency of the vibration system acquired after the scan operation or in the early stage of control using the PLL.

The initial feature value may be a value of a resonance frequency at a certain point in time after the start of output. The initial feature value may be an average value of resonance frequencies within a predetermined period from a certain point in time after the output start. The initial feature value may be an integrated value of resonance frequencies within a predetermined period from a certain point in time after the output start. The initial feature value may be a change amount of the resonance frequency within a predetermined period from a certain point in time after the output start. The initial feature value may be an integrated value of the change amount of the resonance frequency within a predetermined period from a certain point in time after the output start. The initial feature value may be a change rate, that is, a differential value of a resonance frequency at a certain time after the output start. The above initial feature values may be used in combination.

For example, the resonance frequency as the initial feature value becomes low in the second and subsequent treatment since the temperature of the first grasping piece 15 is already high. Further, an average value or an integrated value of resonance frequencies within a predetermined period as the initial feature value is low, for example, in the second and subsequent treatment. Further, the temperature is already high, for example, in the second and subsequent treatment, and a temperature rise rate thereafter becomes lower than that of the first treatment, and thus, a change amount of the resonance frequency, an integrated value of the change amount, or a change rate within a predetermined period as the initial feature value is lower than that of the first treatment. Therefore, a threshold set in Step S4 to be described later is set to be low in such cases.

Further, the certain point in time after the output start herein is appropriately set. For example, the certain point in time may be a point in time when a predetermined period has elapsed from the output start. Various points in time such as a point in time immediately after the scan operation, at a start of the PLL, and a point in time after a lapse of a predetermined time from the start of the PLL can be adopted as the certain point in time after the output start.

In Step S4, the threshold setting unit 43 of the processor 40 sets an operation threshold relating to the resonance frequency serving as a reference for execution of an output reduction operation such as stop of the output based on the calculated initial feature value.

An example of a method of determining the operation threshold will be described. A relationship between the initial feature value and the operation threshold is stored in the storage medium 48 of the energy control device 3, for example. The threshold setting unit 43 determines the operation threshold based on the acquired initial feature value and the relationship between the initial feature value and the operation threshold. The relationship between the initial feature value and the operation threshold may be stored, for example, as a table, and the threshold setting unit 43 may select the operation threshold based on the initial feature value. The relationship between the initial feature value and the operation threshold may be stored as a function, and the threshold setting unit 43 may calculate the operation threshold based on the initial feature value and the function.

The relationship between the initial feature value and the operation threshold may be different for each model of the ultrasonic treatment instrument 2. Therefore, the operation threshold may be set as follows. That is, for example, identification information indicating a model of the ultrasonic treatment instrument 2 is stored in the storage medium 25 of the ultrasonic treatment instrument 2. Further, the relationship between the initial feature value and the operation threshold for each model is stored in the storage medium 48 of the energy control device 3. The threshold setting unit 43 may read the identification information on the model from the storage medium 25 of the ultrasonic treatment instrument 2 and may set the operation threshold based on the relationship between the initial feature value corresponding to the identification information and the operation threshold. Even if the model information of the ultrasonic treatment instrument 2 is not stored in the storage medium 25, for example, different resistors may be provided in the ultrasonic treatment instrument 2 depending on the model of the ultrasonic treatment instrument 2, and the energy control device 3 may acquire a resistance value of the resistor at the time of being connected to the ultrasonic treatment instrument 2 to discriminate the model of the ultrasonic treatment instrument 2. The relationship between the initial feature value and the operation threshold may be stored in the storage medium 25 of the ultrasonic treatment instrument 2, and the threshold setting unit 43 may read the relationship to set the operation threshold.

In Step S5, the output control unit of the processor 40 compares a current resonance frequency of the vibration system with the operation threshold, and determines whether the resonance frequency has fallen below the operation threshold. When the resonance frequency does not fall below the operation threshold, the processing repeats Step S5. That is, the processor 40 continues the output control using the PLL to continue the treatment using the ultrasonic treatment instrument 2. On the other hand, when it is determined that the resonance frequency has fallen below the operation threshold, the process proceeds to Step S6.

Although it is described herein that the resonance frequency has fallen below the operation threshold, the value of the resonance frequency used for comparison is not limited to an instantaneous value but may be a moving average value or the like in order to prevent erroneous determination due to noise or the like.

In Step S6, the output control unit 44 of the processor 40 performs the output reduction operation. The output reduction operation is, for example, an operation of stopping the output of power from the energy output source 50. The output reduction operation may be, for example, an operation of decreasing the output power from the energy output source 50. The output reduction operation may be an operation of notifying the user that the resonance frequency has fallen below the operation threshold using the notification unit 64. This operation may be, for example, display on a display, an output of a notification sound from a speaker, or the like. The output reduction operation may be a combination of the stop or decrease of the output power and the notification. The output control process is ended after the processing of Step S6.

Incidentally, the energy control device 3 may be configured such that the threshold setting unit 43 can change the operation threshold set in Step S4 based on an instruction from the user input via the input unit 62.

The energy control device 3 may be configured such that the threshold setting function based on the initial feature value according to the present embodiment, a type of the operation or presence or absence of the operation when the resonance frequency of the vibration system has fallen below the operation threshold is switched based on an instruction of the user input via the input unit 62.

The case where only one operation threshold is set is illustrated in the above example, but two or more operation thresholds may be set. For example, the energy control device 3 may be configured such that the output is reduced when the resonance frequency has fallen below a first operation threshold and the output is stopped when the resonance frequency has fallen below a second operation threshold which is lower than the first operation threshold.

In the present embodiment, the ultrasonic treatment instrument 2 has been described as the instrument that performs treatment by ultrasonic vibration of the first grasping piece 15, but is not limited thereto. The ultrasonic treatment instrument 2 may have a function as a high-frequency treatment instrument that applies a high-frequency voltage between the first grasping piece 15 and the second grasping piece 16 in addition to the ultrasonic vibration. The high-frequency treatment instrument causes a high-frequency current to flow to a tissue to be treated to perform treatment with heat generated by the current flowing through the tissue. The ultrasonic treatment instrument 2 may be a treatment instrument in which a heater is provided on the first grasping piece 15 or the second grasping piece 16 to treat a tissue to be treated by heat of the heater together with ultrasonic vibration.

According to the treatment system 1 according to the present embodiment, the ultrasonic vibration of the first grasping piece 15 is reduced or stopped when the treatment of the living tissue to be treated has been completed and the tissue has been divided. Therefore, the ultrasonic vibration of the first grasping piece 15 is prevented while the first grasping piece 15 and the pad member 21 of the second grasping piece 16 are in contact with each other. As a result, abrasion or deformation of the pad member 21 is suppressed.

Further, the reduction or stop of the ultrasonic vibration of the first grasping piece 15 is performed based on the relationship between the resonance frequency of the vibration system including the first grasping piece 15 depending on the temperature and the set operation threshold. Here, the operation threshold is set based on the feature value relating to the resonance frequency at the initial stage of the output. Therefore, even when the temperature of the first grasping piece 15 is high to a certain extent from the start of the treatment, for example, in a situation where the treatment is repeatedly performed, the operation threshold is appropriately set. As a result, appropriate treatment can always be performed.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An energy control device that supplies power to an ultrasonic treatment instrument comprising an end effector performing treatment using ultrasonic vibration generated by an ultrasonic transducer, the energy control device comprising:
   an energy source configured to output the power to the ultrasonic transducer; and
   at least one integrated circuit configured to:
      acquire a resonance frequency of a vibration system including the ultrasonic transducer;
      calculate an initial feature value relating to the resonance frequency after a start of an output of the power;
      set a first threshold based on the initial feature value;
      determine whether the resonance frequency has fallen below the threshold; and
      in response to determining that the resonance frequency has fallen below the threshold, perform at least one of (a) causing the energy source to stop or reduce the output of the power to the ultrasonic transducer and (b) notifying that the resonance frequency has fallen below the first threshold; and subsequent to the performing, set a second threshold, the second threshold being a different value from the first threshold.

2. The energy control device according to claim 1, wherein the at least one integrated circuit is configured to calculate the initial feature value based on at least any one of the resonance frequency at a predetermined point in time after the start of the output, a change rate of the resonance frequency at the predetermined point in time, an average value of the resonance frequencies within a predetermined period after the start of the output, an integrated value of the resonance frequencies within the predetermined period, a change amount of the resonance frequency within the predetermined period, and an integrated value of the change amount of the resonance frequency within the predetermined period.

3. The energy control device according to claim 1, further comprising a memory that stores a relationship between the initial feature value and the first threshold, wherein the at least one integrated circuit is configured to set the first threshold based on the calculated initial feature value and the stored relationship.

4. The energy control device according to claim 1, wherein the at least one integrated circuit is configured to calculate the initial feature value at a point in time when a predetermined time has elapsed from the start of the output of the energy source.

5. The energy control device according to claim 1, wherein the at least one integrated circuit is configured to cause the energy source to perform a scan operation to change a frequency of the output in order to acquire the resonance frequency after the start of the output of the energy source and calculate the initial feature value after the scan operation.

6. The energy control device according to claim 1, further comprising an input device that receives an instruction from a user, wherein the at least one integrated circuit is configured to adjust the first threshold based on an input to the input device.

7. The energy control device according to claim 1, further comprising an input device that receives an instruction from a user, wherein the at least one integrated circuit switches a type of an operation or presence or absence of an operation when the resonance frequency and the first threshold satisfy a predetermined relationship based on an input to the input device.

8. A treatment system comprising:

the energy control device according to claim 1;

the ultrasonic transducer configured to be supplied with power from the energy control device; and the ultrasonic treatment instrument.

9. The treatment system according to claim 8, wherein the end effector comprises a first grasping piece configured such that ultrasonic vibration is transmitted and a second grasping piece configured to be opened and closed with respect to the first grasping piece, and the second grasping piece comprises a pad member that is brought into contact with the first grasping piece in a state where the first grasping piece and the second grasping piece is closed.

10. The treatment system according to claim 8, wherein the ultrasonic treatment instrument comprises a memory in which a relationship between the initial feature value and the first threshold is stored, and the at least one integrated circuit is configured to read the relationship from the memory and sets the first threshold using the read relationship when the ultrasonic treatment instrument is connected to the energy control device.

11. The treatment system according to claim 8, wherein the ultrasonic treatment instrument comprises a first memory in which identification information is stored, the energy control device comprises a second memory in which a relationship between the identification information, the initial feature value, and the first threshold is stored, and the at least one integrated circuit is configured to read the identification information from the first memory and sets the first threshold using the relationship stored in the second memory corresponding to the identification information when the ultrasonic treatment instrument is connected to the energy control device.

12. An energy control device comprising:

a processor comprising hardware configured to:

acquire a resonance frequency of an ultrasonic transducer;

calculate an initial feature value relating to the resonance frequency after a start of an output of power;

set a first threshold based on the initial feature value;

determine whether the resonance frequency has fallen below the first threshold; and in response to determining that the resonance frequency has fallen below the first threshold, perform at least one of (a) causing the energy source to stop or reduce the output of the power to the ultrasonic transducer and (b) notifying that the resonance frequency has fallen below the first threshold; and subsequent to the performing, set a second threshold, the second threshold being a different value from the first threshold.

13. The energy control device according to claim 12, further comprising:

an integrated circuit configured to calculate the initial feature value based on at least any one of the resonance frequency at a predetermined point in time after the start of the output, a change rate of the resonance frequency at the predetermined point in time, an average value of the resonance frequencies within a predetermined period after the start of the output, an integrated value of the resonance frequencies within the predetermined period, a change amount of the resonance frequency within the predetermined period, and an integrated value of the change amount of the resonance frequency within the predetermined period.

14. The energy control device according to claim 12, further comprising:

a memory that stores a relationship between the initial feature value and the first threshold; and an integrated circuit configured to set the first threshold based on the calculated initial feature value and the stored relationship.

15. The energy control device according to claim 12, further comprising:
- an input device that receives an instruction from a user; and
- an integrated circuit configured to switch a type of an operation or presence or absence of an operation when the resonance frequency and the first threshold satisfy a predetermined relationship based on an input to the input device.

16. A treatment system comprising:
- the energy control device according to claim 12;
- the ultrasonic transducer configured to be supplied with power from the energy control device; and
- an ultrasonic treatment instrument.

17. The treatment system according to claim 16, further comprising:
- an end effector comprising a first grasping piece configured such that ultrasonic vibration is transmitted and a second grasping piece configured to be opened and closed with respect to the first grasping piece, wherein:
- the second grasping piece comprises a pad member that is brought into contact with the first grasping piece in a state where the first grasping piece and the second grasping piece is closed.

18. The treatment system according to claim 16, wherein
- the ultrasonic treatment instrument comprises a memory in which a relationship between the initial feature value and the first threshold is stored, and
- an integrated circuit is configured to read the relationship from the memory and sets the first threshold using the read relationship when the ultrasonic treatment instrument is connected to the energy control device.

19. The treatment system according to claim 16, wherein:
- the ultrasonic treatment instrument comprises a first memory in which identification information is stored,
- the energy control device comprises a second memory in which a relationship between the identification information, the initial feature value, and the first threshold is stored, and
- an integrated circuit is configured to read the identification information from the first memory and sets the first threshold using the relationship stored in the second memory corresponding to the identification information when the ultrasonic treatment instrument is connected to the energy control device.

* * * * *